United States Patent [19]

Baker et al.

[11] 3,971,850

[45] July 27, 1976

[54] N-SUBSTITUTED-N-(1-SUBSTITUTED-1-METHYL-2-PROPYNYL)-α-(SUBSTITUTED PHENOXY) ALKYLAMIDES AND THEIR USE AS MITICIDES

[75] Inventors: Don R. Baker, Orinda; Francis H. Walker, Mill Valley, both of Calif.

[73] Assignee: Stauffer Chemical Company, Westport, Conn.

[22] Filed: June 30, 1975

[21] Appl. No.: 591,665

[52] U.S. Cl. ............................. 424/324; 260/559 B
[51] Int. Cl.² .................... A01N 9/20; C07C 103/19
[58] Field of Search ................ 260/559 B; 424/324

[56] References Cited
UNITED STATES PATENTS

| | | | |
|---|---|---|---|
| 2,426,885 | 9/1947 | Kilgore | 424/320 |
| 3,557,209 | 1/1971 | Richter et al. | 260/559 B |

*Primary Examiner*—Leonard Schenkman
*Attorney, Agent, or Firm*—Michael J. Bradley

[57] ABSTRACT

Miticidally active compounds are described herein, which are defined by the generic formula

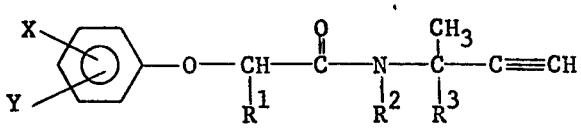

wherein X is either fluorine or trifluoromethyl; Y is either hydrogen or chlorine; $R^1$ is either methyl or ethyl; and where X is fluorine, $R^2$ is hydrogen and $R^3$ is methyl; and where X is trifluoromethyl, $R^2$ and $R^3$ are independently either hydrogen or methyl.

18 Claims, No Drawings

N-SUBSTITUTED-N-(1-SUBSTITUTED-1-METHYL-2-PROPYNYL)-α-(SUBSTITUTED PHENOXY) ALKYLAMIDES AND THEIR USE AS MITICIDES

BACKGROUND OF THE INVENTION

Various substituted amides, particularly N-substituted amides and substituted phenoxy amides, are known to be useful as insecticides, miticides, and herbicides. Typical insecticidal properties of such compounds are taught in U.S. Pat. No. 2,426,885 and its two continuations-in-part, U.S. Pat. No. 2,484,295 and U.S. Pat. No. 2,484,296. Herbicidal properties of such compounds are taught in U.S. Pat. Nos. 3,272,844, 3,439,018, and 3,564,607, and Belgian Pat. No. 739,714.

BRIEF DESCRIPTION OF THE INVENTION

This invention relates to a novel class of substituted acetylenic amides and to their use as miticides when used in a miticidally effective amount. More specifically, this invention relates to N-substituted-N-(1-substituted-1-methyl-2-propynyl)-α-(substituted phenoxy) alkylamides having the formula

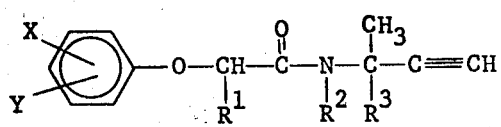

wherein X is either fluorine or trifluoromethyl; Y is either hydrogen or chlorine; $R^1$ is either methyl or ethyl; and where X is fluorine, $R^2$ is hydrogen and $R^3$ is methyl; and where X is trifluoromethyl, $R^2$ and $R^3$ are independently either hydrogen or methyl.

By "miticidally effective amount" is meant the amount of the herein disclosed miticidal compounds which when applied to the habitat of mites in any conventional manner will kill or substantially injure a significant portion of the population thereon.

DETAILED DESCRIPTION OF THE INVENTION

The compounds of the present invention can be prepared by the following general method, wherein X, Y, $R^1$, $R^2$ and $R^3$ are as defined above:

Reaction No. 1

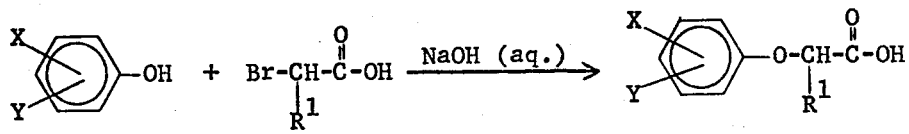

To a mixture of a molar amount of the phenol and a slight molar excess of the acid is added a slight molar excess of 50% aqueous NaOH. The product acid is then washed with suitable solvents and recovered from the organic phase.

Reaction No. 2

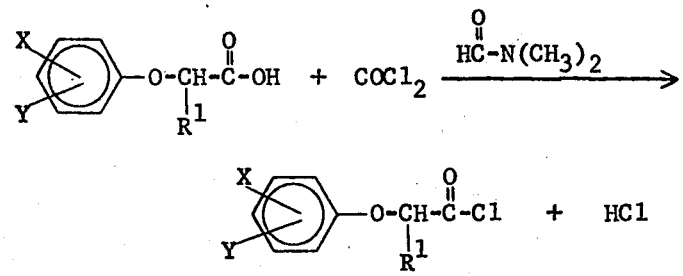

A slight molar excess of phosgene is introduced into a molar amount of the acid in a suitable solvent, to which a small amount of dimethyl formamide has been added. The excess phosgene and HCl are removed and the solvent is evaporated to leave the acid chloride.

Reaction No. 3

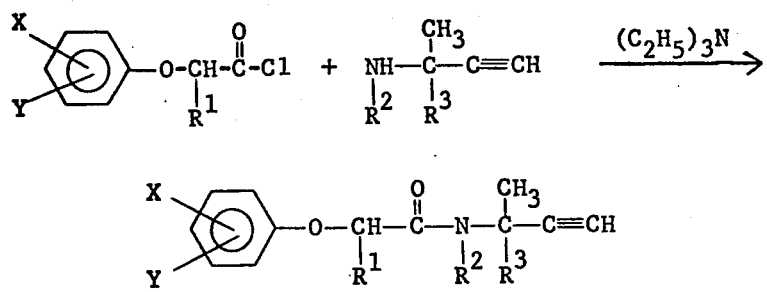

The acid chloride is added to a solution containing both the acetylenic amine and the triethylamine at 10°–15°C. After successive washings, the product is recovered from the organic phase.

As an alternative to the above general method, the following method may be used:

Reaction No. 1'

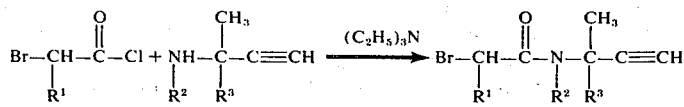

The procedure for this reaction is similar to that for Reaction No. 3 above.

Reaction No. 2'

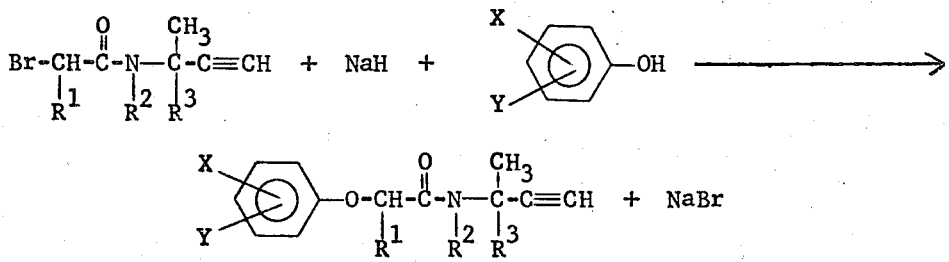

Under an inert atmosphere, a molar amount of the phenol in a suitable solvent is added to a slight molar excess of the sodium hydride suspended in the solvent. A slight molar excess of the amide, also dissolved in the solvent, is then added. After the reaction, the mixture is filtered, and the product phenoxyalkylamide is recovered from the filtrate.

The examples shown herein are illustrative of the method of preparation of the compounds of the invention.

EXAMPLE I

N-dimethylpropynyl-α-(4-fluorophenoxy)butyramide. (Compound No. 1 in Table I below.

2-bromobutyryl chloride, 25.0 g (0.12 mole), in 25 ml methylene chloride was added dropwise to a mixture of 12.5 g (0.15 mole) dimethylpropargylamine and 15.2 g (0.15 mole) triethylamine in 175 ml methylene chloride with stirring. The mixture was maintained at a temperature of 5°–10°C by a cold water bath. The cold bath was removed after the acid chloride addition was complete. After allowing the solution to stand for one-half hour, the mixture was washed with 100 ml water, followed by two 100 ml portions of dilute sulfuric acid and two 100 ml portions of sodium bicarbonate solution. Removal of the solvent in a vacuum left 23.5 g (79% yield) of a solid which was N-dimethylpropynyl-2-bromobutyramide, identified by a melting point of 80°–84°C.

0.8 g (0.035 mole) of sodium hydride was suspended in 25 ml of anhydrous tetrahydrofuran in a 300 ml flask which was fitted with a thermometer, a reflux condenser with drying tube, an argon inlet and a stirrer. 3.4 g (0.030 mole) p-fluorophenol in 25 ml tetrahydrofuran was added dropwise to the suspension while the reaction vessel was swept with argon. At the completion of the phenol addition, the mixture was allowed to stand for a half hour. 7.4 g (0.030 mole) N-dimethylpropynyl-2-bromobutyramide in 50 ml tetrahydrofuran was then added to the mixture in several portions. The mixture was heated at reflux for 1 hour, cooled and filtered through a pad of Celite. The filtrate was evaporated and the residue was dissolved in 100 ml methylene chloride. The solution was washed with water, followed by two 100 ml portions of diluted HCl and two 100 ml portions of 5% $Na_2CO_3$ solution. The solution was dried over $MgSO_4$ and evaporated to leave 6.1 g (77.2% crude yield) of a solid which was recrystallized from hexane to give 3.2 g of a solid identified by infrared spectroscopy to be N-dimethylpropynyl-2-(4-fluorophenoxy)butyramide, m.p. 72°–75°C.

EXAMPLE II

N-methyl-N-methylpropynyl-α-(3-trifluoromethylphenoxy)-butyramide. (Compound No. 3 in Table I below).

To a mixture of 50 g (0.31 mole) α,α,α-trifluoro-m-cresol and 60.1 g (0.36 mole) 2-bromobutyric acid was added 61.6 g (0.77 mole) 50% aqueous sodium hydroxide with rapid stirring at an initial temperature of 15°C. The temperature rose to 45°C over the course of the addition and was held between 15°C and 45°C with a cold water bath. At the completion of the sodium hydroxide addition, the cold bath was removed and the mixture was heated to 110°C for 15 minutes. Then 80 ml water, 80 ml perchloroethylene, and 65 ml concentrated hydrochloric acid were added to the reaction mixture and the mixture was heated to 85°C, then phase separated. The organic layer was cooled and the product, α-(3-trifluoromethylphenoxy)-butyric acid, crystallized. The acid was removed by filtration to give 72.2 g (90% crude yield) of a solid, which was recrystallized from hexane to give 60 g of the acid, identified by its melting point, 65°–70°C.

0.2 g dimethyl formamide was added to a slurry of 60 g (0.23 mole) of α-(3-trifluoromethylphenoxy) butyric acid in 100 ml toluene. The slurry was then heated to 60°C in a 500 ml flask which was fitted with a gas inlet tube, a stirrer, a thermometer, and a dry ice-isopropyl alcohol condenser. 33 g (0.33 mole) phosgene was passed into the mixture at a moderate rate. The dry ice condenser was then removed and replaced with a water cooled condenser. Excess phosgene and HCl were removed by purging the solution with argon at 60°C. The solution was then cooled, and the solvent was removed in vacuum to leave an oil, 61.1 g (99.7% yield), which was α-(3-trifluoromethylphenoxy)-butyryl chloride.

8.0 g (0.03 mole) of the acid chloride was added dropwise to a mixture of N-methyl-2-amino-3-butyne, 2.9 g (0.035 mole), and triethylamine, 3.6 g (0.035 mole), in 100 ml methylene chloride at 10°–15°C. Some cooling in an ice bath was necessary to maintain the temperature. After the addition of the acid chloride, the mixture was allowed to come to room temperature and the product was isolated by washing with, in succession, 100 ml portions of water, dilute HCl, 5% $Na_2CO_3$ solution, and water. The organic phase was dried over magnesium sulfate and the solvent was removed in vacuum to leave an oil, 7.9 g (84% yield), $n_D^{30}$ 1.4779, identified by infrared spectroscopy as N-methyl-N-methylpropynyl-α-(3-trifluoromethylphenoxy)-butyramide.

Other compounds, such as those included in the following table, can be prepared in a manner analogous to that shown in the examples above, starting with the appropriate materials. The compounds in the table are representative of those embodied in the present invention. Compound numbers have been assigned to them for use as identification throughout the balance of the specification.

and seven days later mortality is determined for both the adult mites and the nymphs hatching from eggs which were on the plants at the time of treatment. Test concentrations range from 0.05% down to that at which 50% mortality occurs (LD-50).

II. Systemic Assay

Test chemicals are dissolved in acetone and aliquots are diluted in 200 cc of water in glass bottles. Two pinto bean plants (*Phaseolus sp.*), with expanded primary leaves, are supported in each bottle by cotton plugs, so that their roots and stems are immersed in the treated water. The plants are then infested with 75–100 two-spotted mites of various ages and sexes. One week later the mortality of the adult mites and nymphs is recorded. Test concentrations range from 10 ppm down to that at which 50% mortality occurs (LD-50).

TABLE I

| COMPOUND NUMBER | COMPOUND |
| --- | --- |
| 1 | F—C₆H₄—O—CH(C₂H₅)—C(=O)—NH—C(CH₃)₂—C≡CH |
| 2 | (3-CF₃)C₆H₄—O—CH(C₂H₅)—C(=O)—NH—C(CH₃)₂—C≡CH |
| 3 | (3-CF₃)C₆H₄—O—CH(C₂H₅)—C(=O)—N(CH₃)—CH(CH₃)—C≡CH |
| 4 | (Cl, CF₃)C₆H₃—O—CH(C₂H₅)—C(=O)—NH—C(CH₃)₂—C≡CH |
| 5 | (F, Cl)C₆H₃—O—CH(C₂H₅)—C(=O)—NH—C(CH₃)₂—C≡CH |
| 6 | F—C₆H₄—O—CH(CH₃)—C(=O)—NH—C(CH₃)₂—C≡CH |

Miticidal activity on the two-spotted mite [*Tetranychus urticae* (Koch)] was evaluated as follows:

I. Plant Dip Assay

Pinto bean plants (*Phaseolus sp.*), approximately 10 cm tall, are transplanted into sandy loam soil in 3-inch clay pots and thoroughly infested with two-spotted mites of mixed ages and sexes. Twenty-four hours later the infested plants are inverted and dipped for 2–3 seconds in 50–50 acetone-water solutions of the test chemicals. Treated plants are held in the greenhouse, The following is a table of examples of the utility of certain of the compounds of the invention as miticides, indicating the effective concentration at which LD-50 control effect was achieved.

TABLE II

| Effective Concentrations on Two-Spotted Mite [*Tetranychus urticae* (Koch)] | | | |
| --- | --- | --- | --- |
| COMPOUND NUMBER | PF. (%) | Eggs (%) | SYS (ppm) |
| 1 | .05 | >.05 | — |

TABLE II-continued

| | Effective Concentrations on Two-Spotted Mite [Tetranychus urticae (Koch)] | | |
|---|---|---|---|
| COMPOUND NUMBER | PE (%) | Eggs (%) | SYS (ppm) |
| 2 | .03 | >.05 | 8 |
| 3 | .03 | >.05 | >10 |

PE = Post-embryonic
SYS = Systemic
> = Greater than

Neither the examples nor the tables hereinabove are intended to limit the invention in any manner.

The compounds of this invention are generally embodied in a form suitable for convenient application. For example, the compounds can be embodied in miticidal compositions in the form of emulsions, suspensions, solutions, dusts, and aerosol sprays. In addition to the active compounds, such compositions generally contain the adjuvants which are normally found in miticide preparations. One such composition can contain either a single miticidally active compound or a combination of miticidally active compounds. The miticide compositions of this invention can contain as adjuvants organic solvents such as sesame oil, xylene, or heavy petroleum; water; emusifying agents; surface active agents; talc; pyrophyllite; diatomite; gypsum; clays; or propellants such as dichlorodifluoromethane; or a combination of these. If desired, however, the active compounds can be applied directly to feedstuffs, seeds, or other such matter upon which the pests feed. When applied in such a manner, it will be advantageous to use a compound which is not volatile. In connection with the activity of the presently disclosed miticidal compounds, it should be fully understood that the compounds need not be active as such. The purposes of this invention will be fully served by a compound which is rendered active by an external influence such as light, or by some physiological action which the compound induces when it is ingested into the body of the pest.

The precise manner in which the miticidal compounds of this invention should be used in any particular instance will be readily apparent to a person skilled in the art. The concentration of the active miticide in a typical composition can vary within rather wide limits. Ordinarily, the miticide will comprise not more than about 15.0% by weight of the composition. The preferred range of concentration of the miticide is about 0.1 to about 1.0% by weight.

We claim:
1. A compound having the formula

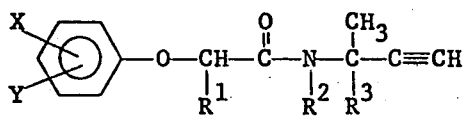

wherein X is either fluorine or trifluoromethyl; Y is either hydrogen or chlorine; $R^1$ is either methyl or ethyl; and where X is fluorine, $R^2$ is hydrogen and $R^3$ is methyl; and where X is trifluoromethyl, $R^2$ and $R^3$ are independently selected from the group consisting of hydrogen and methyl.

2. A compound according to claim 1 in which $R^1$ is ethyl.
3. A compound according to claim 1 in which X is fluorine.
4. A compound according to claim 1 in which $R^1$ is ethyl and X is fluorine.
5. A compound according to claim 4 in which X is 4-fluoro, and Y is hydrogen.
6. A compound according to claim 1 in which X is trifluoromethyl.
7. A compound according to claim 1 in which X is trifluoromethyl, and $R^1$ is ethyl.
8. A compound according to claim 7 in which X is 3-trifluoromethyl, Y is hydrogen, $R^2$ is hydrogen, and $R^3$ is methyl.
9. A compound according to claim 7 in which X is 3-trifluoromethyl, Y is hydrogen, $R^2$ is methyl, and $R^3$ is hydrogen.
10. A method of controlling mites comprising applying to the habitat thereof a miticidally effective amount of a compound having the formula

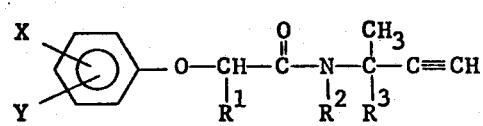

wherein X is either fluorine or trifluoromethyl; Y is either hydrogen or chlorine; $R^1$ is either methyl or ethyl; and where X is fluorine, $R^2$ is hydrogen and $R^3$ is methyl; and where X is trifluoromethyl, $R^2$ and $R^3$ are independently selected from the group consisting of hydrogen and methyl.

11. A method according to claim 10 in which $R^1$ is ethyl.
12. A method according to claim 10 in which X is fluorine.
13. A method according to claim 10 in which $R^1$ is ethyl and X is fluorine.
14. A method according to claim 13 in which X is 4-fluoro, and Y is hydrogen.
15. A method according to claim 10 in which X is trifluoromethyl.
16. A method according to claim 10 in which X is trifluoromethyl, and $R^1$ is ethyl.
17. A method according to claim 16 in which X is 3-trifluoromethyl, Y is hydrogen, $R^2$ is hydrogen, and $R^3$ is methyl.
18. A method according to claim 16 in which X is 3-trifluoromethyl, Y is hydrogen, $R^2$ is methyl, and $R^3$ is hydrogen.

* * * * *